(12) United States Patent
Kokubo

(10) Patent No.: US 7,811,518 B2
(45) Date of Patent: Oct. 12, 2010

(54) SAMPLE SLICE PREPARATION DEVICE AND SAMPLE SLICE PREPARATION METHOD

(75) Inventor: Mitsunori Kokubo, Numazu (JP)

(73) Assignee: Toshiba Kikai Kabushiki Kaisha, Tokyo (JP)

( * ) Notice: Subject to any disclaimer, the term of this patent is extended or adjusted under 35 U.S.C. 154(b) by 1083 days.

(21) Appl. No.: 11/465,024

(22) Filed: Aug. 16, 2006

(65) Prior Publication Data

US 2007/0039435 A1    Feb. 22, 2007

(30) Foreign Application Priority Data

Aug. 22, 2005 (JP) ............................. 2005-239952

(51) Int. Cl.
*G01N 21/00* (2006.01)
(52) U.S. Cl. .............................. 422/65; 422/63; 422/64; 422/66; 422/99; 422/100; 436/180; 83/13
(58) Field of Classification Search ............. 422/63–67, 422/99–100; 436/180; 83/13
See application file for complete search history.

(56) References Cited

U.S. PATENT DOCUMENTS 5,156,019 A    10/1992    McCormick

FOREIGN PATENT DOCUMENTS

| EP | 1498718 | 1/2005 |
|---|---|---|
| JP | 06-323967 | 11/1994 |
| JP | 2002-022626 | 1/2002 |
| JP | 2003-294591 | 10/2003 |
| JP | 2004-28910 | 1/2004 |
| JP | 2004-028965 | 1/2004 |
| JP | 2005-079362 | 3/2005 |

OTHER PUBLICATIONS

Office Action issued in corresponding JP 2005-239952 on Jul. 8, 2010.
English Translation of Office Action issued in corresponding JP 2005-239952 on Jul. 8, 2010.
English Language Abstract of JP 06-323967 issued on Nov. 25, 1994.
Machine English Language Translation of JP 06-323967 issued on Nov. 25, 1994.

(Continued)

*Primary Examiner*—Jyoti Nagpaul
(74) *Attorney, Agent, or Firm*—DLA Piper LLP US

(57) ABSTRACT

A sample slice preparation device of the present invention has a microtome which slices a solid specimen by a knife, a humidifier which imparts moisture to a carrier tape, slice conveyer means for adsorbing a slice by an adsorbing force of moisture imparted to the carrier tape to feed out the slice, transfer mechanism for applying water to the surface of a slide glass to transfer the slice from the carrier tape onto the slide glass by an adsorbing force of applied water, an extension unit which heats the slide glass having the slice adsorbed thereon to evaporate the moisture, thereby extending the slice, and slide glass conveyer means for conveying the slide glass provided with the slice.

7 Claims, 8 Drawing Sheets

OTHER PUBLICATIONS

English Language Abstract of JP 2003-294591 issued on Oct. 15, 2003.
Machine English Language Translation of JP 2003-294591 issued on Oct. 15, 2003.
English Language Abstract of JP 2002-22626 issued on Jan. 23, 2002.
Machine English Language Translation of JP 2002-022626 issued on Jan. 23, 2002.
English Language Abstract of JP 2005-079362 issued on Mar. 24, 2005.
Machine English Language Translation of JP 2005-079362 issued on Mar. 24, 2005.

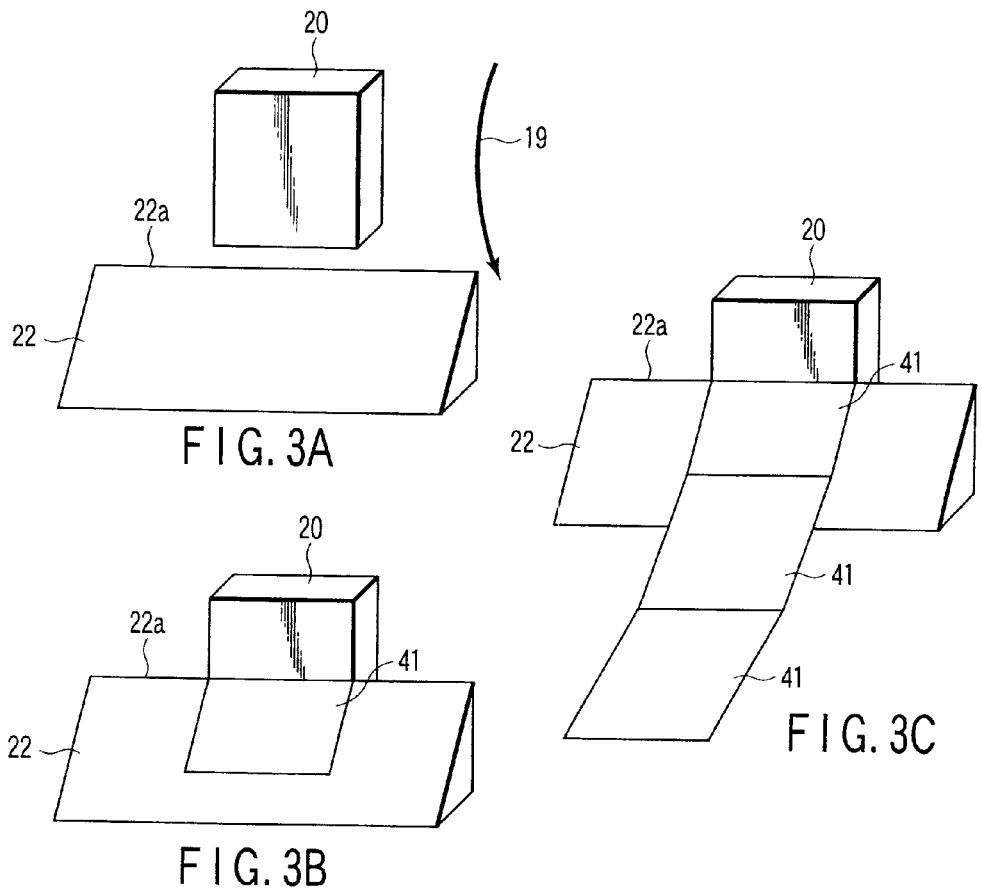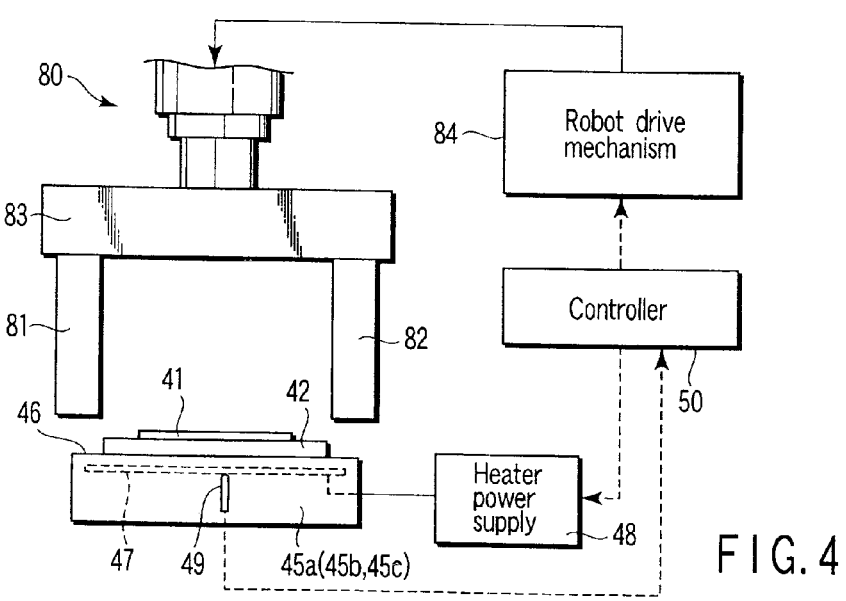

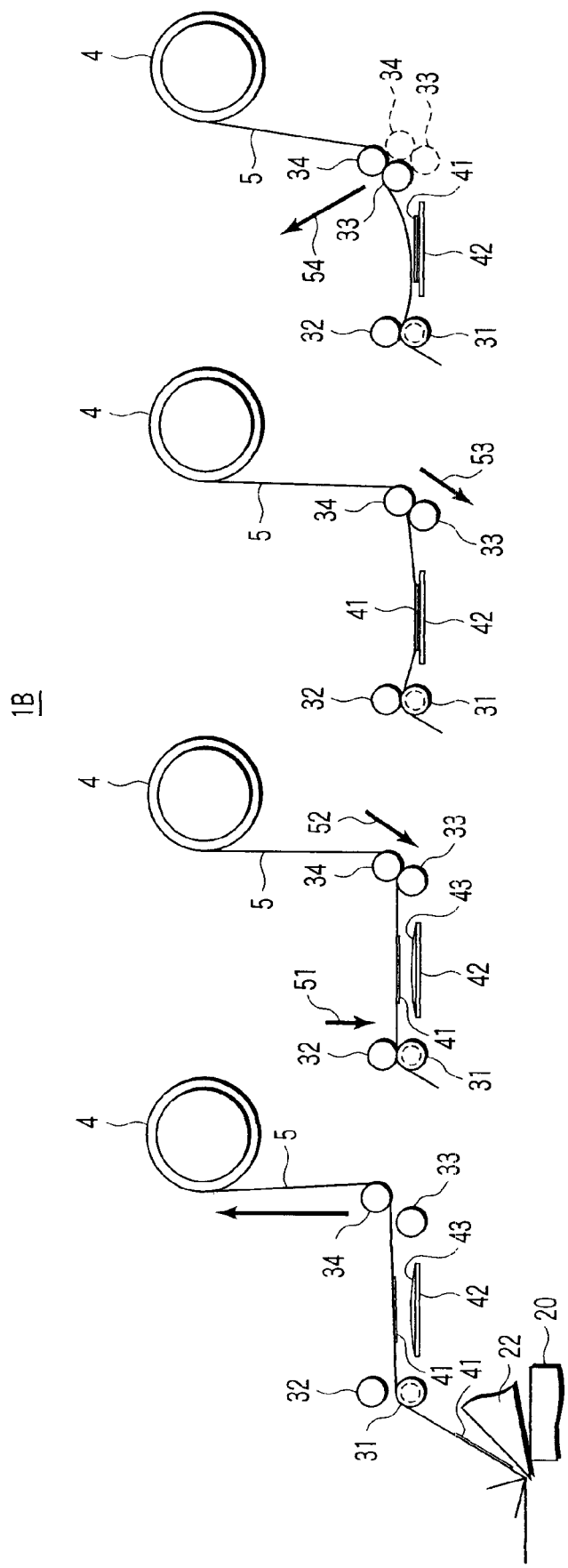

SAMPLE SLICE PREPARATION DEVICE AND SAMPLE SLICE PREPARATION METHOD

CROSS-REFERENCE TO RELATED APPLICATIONS

This application is based upon and claims the benefit of priority from prior Japanese Patent Application No. 2005-239952, filed Aug. 22, 2005, the entire contents of which are incorporated herein by reference.

BACKGROUND OF THE INVENTION

1. Field of the Invention

The present invention relates to a microtome for use in scientific specimen analysis or medical analysis such as microscopic observation of a living specimen, more particularly to a device and a method in which a specimen slice is taken out onto an auxiliary slicing member by use of moisture, and thereafter the slice taken out onto the auxiliary slicing member is brought into contact (pressed with a microforce) with a slide glass coated with water. The only slice is transferred from the auxiliary slicing member to the slide glass, and warmed (heated) for a fixed time, crease or shrinkage generated in the slice during slicing is eliminated, a close contact fixing force with respect to the slide glass is enhanced, and a satisfactory sample slice is prepared.

2. Description of the Related Art

Heretofore, an operation to prepare (cut out) a slice is performed by an operator by use of a microtome (device in which after moving a solid specimen or a knife as much as an amount corresponding to a desired cut thickness, the solid specimen is sliced by the knife to prepare the slice). The solid specimen includes a frozen specimen embedded using a freezing embed material, and a paraffin embedded specimen using paraffin, and the microtome to perform the slicing includes a sliding microtome and a rotary microtome. In a step of preparing this slice, an important and very difficult point is handling of the slice during cutting and after end of a cutting step.

There will be described a conventional slice sampling method using the sliding microtome with reference to FIGS. 10A, 10B and 10C.

First, as shown in FIG. 10A, a cutting blade 22 is fed in an arrow direction in the diagram, and slicing of a solid specimen 20 is started. Instead of the cutting blade 22, the solid specimen 20 may be moved toward the cutting blade 22. As shown in FIG. 10B, while moving the cutting blade 22 with one hand, an operator, with the other hand, brings a distant end portion of a jig 23 (there may be used another jig such as a small paper-made moisture-containing strip or a wooden pencil-like jig having its distant end sharpened) such as a very thin moisture-containing brush into contact with a cut start edge of a slice 41 generated at this time.

Next, as shown in FIG. 10C, while moving the jig 23 brought into contact with the slice 41 at a speed equal to that to move the cutting blade 22 as it is, the cutting is ended, whereby it is possible to take out the slice 41 in a state in which one end of the slice is brought into contact with the jig 23 at the end of the cutting. Moreover, the taken slice 41 is mounted on the slide glass. In general, after floating the slice 41 once on the water surface for a purpose of eliminating the crease or the shrinkage of the taken slice 41, the slice is scooped with the slide glass.

Thereafter, the slide glass to which the slice 41 is attached is mounted on an extension unit (unit such as a hot plate) or disposed in a constant-temperature tank, and warmed (heated) for a certain time, and a non-dyed sample slice is finished. Finally, the sample is subjected to a dyeing step and a sealing step of covering the sample with cover glass to obtain the dyed sample slice.

Next, there will be described a conventional slice sampling method using the rotary microtome with reference to FIGS. 3A, 3B and 3C.

As shown in FIG. 3A, a solid specimen 20 is fed in a direction of an arrow 19 toward a blade edge 22a of a knife 22, and slicing of the solid specimen 20 is started. As shown in FIG. 3B, the blade edge 22a is relatively moved substantially parallel to a main surface of the solid specimen 20, and a slice 41 having a thickness of several microns is cut out. When this is repeated, as shown in FIG. 3C, the slices 41 are continuously generated.

Since the resultant slice 41 usually rounds or creases, the slice is treated into a state in which the slice is to be dyed in accordance with the following treatment procedure.

The resultant slice 41 is attached to a paper slice having one end wetted, and sampled, and the slice 41 having its backside directed to the water surface is floated and extended in water of a water tank. Accordingly, fine creases of the slice 41 are removed. In accordance with a type of the slice 41, water in the water tank may sometimes be warm water at 40 to 45° C.

When the slice floated in the water tank is sufficiently extended, one end of the slide glass is obliquely submerged in water. While one end of the slice is attached to the slide glass, and pressed with a jig such as a tip of a thin brush, the continuous slice 41 is broken in a desired place, and this is put on the slide glass as if it were scooped with the slide glass (attaching step).

The slide glass to which the tissue slice has been attached is mounted on an extension plate, extended and dried. The slice can be dried using the hot plate as the extension plate, while a temperature of the surface of the plate is controlled at, for example, 40 to 45° C. Alternatively, the slide glass to which the slice has been attached may be disposed in the constant-temperature tank, and warmed (heated) for a certain time. This extension treatment is performed to thereby remove further fine creases from the slice, and a close contact strength between the slice and the slide glass can be enhanced (extension step). In this manner, the non-dyed sample slice is formed, and finally subjected to the dyeing step and the sealing step of covering the sample with the cover glass, and the dyed sample slice is finished.

In a case where the sample slice is prepared as described above, since most of the operation depends on a manual operation of a person such as a clinical laboratory technologist, there are various problems such as the following 1 to 5.

1) Since sophisticated skill and technology are required for the operation, the person who performs the operation is limited to an only skilled person.

2) In a case where a large number of slices produced, and a large number of samples are prepared, much labor and time are required.

3) Since the operation demands care, the person remarkably fatigues.

4) Since the person performs the manual operation, it is difficult to prepare a large number of samples with stable precision and quality.

5) Since the person performs the manual operation, a force to be applied to the knife or the like changes, and disadvantages such as thickness unevenness, crease and break are easily generated. Especially, when the person gets tired from a long-time operation, various disadvantages such as the crease, the break and the shrinkage are easily generated.

To solve the problem, for a purpose of solving the above problem by reducing a ratio of the dependence on the manual operation to reduce a burden on the operator, there is proposed a technology in which a part performed by the manual operation is automated and performed by a machine. For example, in paragraphs [0030] to [0032] of Jpn. Pat. Appln. KOKAI Publication No. 2004-28910 (hereinafter referred to as Patent Document 1), an automated device is described in which the slice is electrostatically adsorbed by a carrier tape and conveyed, and the slice is pressed onto an adhesive liquid on the slide glass in a transfer stage to transfer the slice.

However, the device of Patent Document 1 is useful in a case where the specimen is hardened with paraffin or the like, but in a case where a frozen specimen is sliced to prepare the slice, since the specimen is not dried, an electrostatic adsorbing force weakens, and the device is not effective. In addition, since the specimen for preparing the sample slice is constituted by freezing and hardening the moisture-containing slice in many cases, it is difficult to handle the sample, and very much labor and time are required for the operation.

BRIEF SUMMARY OF THE INVENTION

The present invention has been developed to solve the above problem, and an object of the present invention is to provide a sample slice preparation device and a sample slice preparation method having an excellent handling performance, in which crease and shrinkage generated in a sample slice difficult to handle, especially, a slice obtained by slicing a solid specimen brought into a frozen state are eliminated, and a close contact fixing force with respect to a slide glass is enhanced, and it is possible to reduce a ratio of dependence on a manual operation.

The sample slice preparation device of the present invention is a device which slices, by a knife, a solid specimen constituted by embedding an original sample as a slice object with an embedding material to prepare a sample slice, the device comprising: a slicing unit which moves the solid specimen and the knife with respect to each other to slice the solid specimen into a predetermined slice thickness by the knife; moisture imparting means for imparting moisture to a tape-like auxiliary slicing member; slice conveyance means for adsorbing the resultant slice by an adsorbing force of the moisture imparted to the auxiliary slicing member to feed out the slice; transfer means for applying water to the surface of a slide glass to transfer the slice from the auxiliary slicing member onto the slide glass by the adsorbing force of applied water; an extension unit to heat the slide glass by which the slice has been adsorbed and to evaporate the moisture, thereby extending the slice; and slide glass conveyance means for conveying the slide glass provided with the slice.

As the moisture imparting means, a humidifier may be used which sprays mist-like water toward the auxiliary slicing member, or a cooler may be used which locally cools the auxiliary slicing member and a peripheral region of the member to condensate moisture in the atmosphere onto the auxiliary slicing member.

As the transfer means, a water dripping mechanism may be used which drips warm water at a temperature of 30 to 50° C. onto the slide glass. Alternatively, after the transfer means drips and applies water at room temperature onto the slide glass, the extension unit may heat water on the slide glass to obtain warm water at 30 to 50° C. If water heating temperature is less than 30° C., there is not any difference from room temperature, and an effect of promoting the drying is hardly recognized. On the other hand, if the water heating temperature exceeds 50° C., the slice as a living specimen might be modified.

Furthermore, there may be disposed control means for controlling the slice conveyance means to feed out the auxiliary slicing member at a speed ratio of 80 to 90% with respect to a slicing speed of the slicing unit, after one end of the slice is adsorbed by the auxiliary slicing member. If a speed ratio (V2/V1)×100 of an auxiliary slicing member conveyance speed V2 with respect to a slicing speed V1 is below 80%, crease or shrinkage is easily generated in the slice, a shape of the slice deteriorates, and additionally thickness of the slice becomes non-uniform. On the other hand, if the speed ratio (V2/V1)×100 is above 90%, slippage is easily generated between the slice and the auxiliary slicing member, and the slice is inhibited from being smoothly transferred from a solid specimen side to an auxiliary slicing member side, or a local tensile force acts on the slice, and the slice is easily broken.

Furthermore, it is preferable that the control means controls the slide glass conveyance means to take out the slide glass provided with the slice from the extension unit, after the slide glass provided with the slice is heated by the extension unit. In this case, automation of a sample slice preparing operation is further promoted.

A sample slice preparation method of the present invention is a method which slices, by a knife, a solid specimen constituted by embedding an original sample as a slice object with an embedding material to prepare a sample slice, the method comprising: (i) imparting moisture to a tape-like auxiliary slicing member; (ii) adsorbing an end portion of the slice generated in a case where slicing of the solid specimen is started by the knife by the auxiliary slicing member to which the moisture has been imparted, successively transferring the slice from the solid specimen toward the auxiliary slicing member by an adsorbing force of the imparted moisture, continuously bringing the slice continuously generated by further continuing the slicing of the solid specimen into close contact with the auxiliary slicing member to which the moisture has been imparted, and taking out the whole completed slice onto the auxiliary slicing member; (iii) wetting the surface of a slide glass with water, bringing the slice taken out onto the auxiliary slicing member into close contact with this slide glass, and transferring the slice from the auxiliary slicing member onto the slide glass; and (iv) heating the slide glass provided with the slice to evaporate water, thereby extending the slice.

When the solid specimen is fed toward the knife and sliced, the feeding of the tape-like auxiliary slicing member is brought into a stopped state. In a case where the solid specimen is sliced, when the solid specimen is fed, the slice extends upwards to the auxiliary slicing member. At the same time or immediately after a distant end of the slice comes into contact with the auxiliary slicing member, the feeding of the auxiliary slicing member restarts (see FIGS. 2C and 2D). This timing to restart the feeding of this tape may be set to a timing after a predetermined time uniformly elapses from a time when the feeding of the tape stops, a timing at which it is detected by a sensor that the distant end of the slice comes into contact with the auxiliary slicing member, or a timing after a predetermined time uniformly elapses from the detection timing. It is to be noted that in the step (ii), it is preferable that after one end of the slice is adsorbed by the auxiliary slicing member, the auxiliary slicing member is fed out at a speed ratio of 80 to 90% with respect to the slicing speed. The reason has been described above.

In the step (i), mist-like water may be sprayed from a humidifier as moisture imparting means toward the auxiliary slicing member. Alternatively, the auxiliary slicing member and a peripheral region of the member may locally be cooled by a cooler as the moisture imparting means to condensate moisture in the atmosphere onto the auxiliary slicing member.

Moreover, in the step (iii), warm water at a temperature of 30 to 50° C. may be dripped and applied onto the slide glass by use of a water dripping mechanism as transfer means. Alternatively, after the transfer means drips and applies water at room temperature onto the slide glass, an extension unit heats water on the slide glass to obtain warm water at 30 to 50° C.

BRIEF DESCRIPTION OF THE SEVERAL VIEWS OF THE DRAWING

FIGS. 3A to 3C are step diagrams showing a procedure to sample a slice by use of a rotary microtome;

FIG. 4 is a diagram showing a part of a conveyance robot for use in the device of the present invention;

FIGS. 8A to 8D are step diagrams showing a procedure to transfer a slice onto a slide glass by use of the sample slice preparation device in the second embodiment of the present invention;

DETAILED DESCRIPTION OF THE INVENTION

A best mode for carrying out the present invention will be described hereinafter with reference to the accompanying drawings.

FIRST EMBODIMENT

Figure 1:
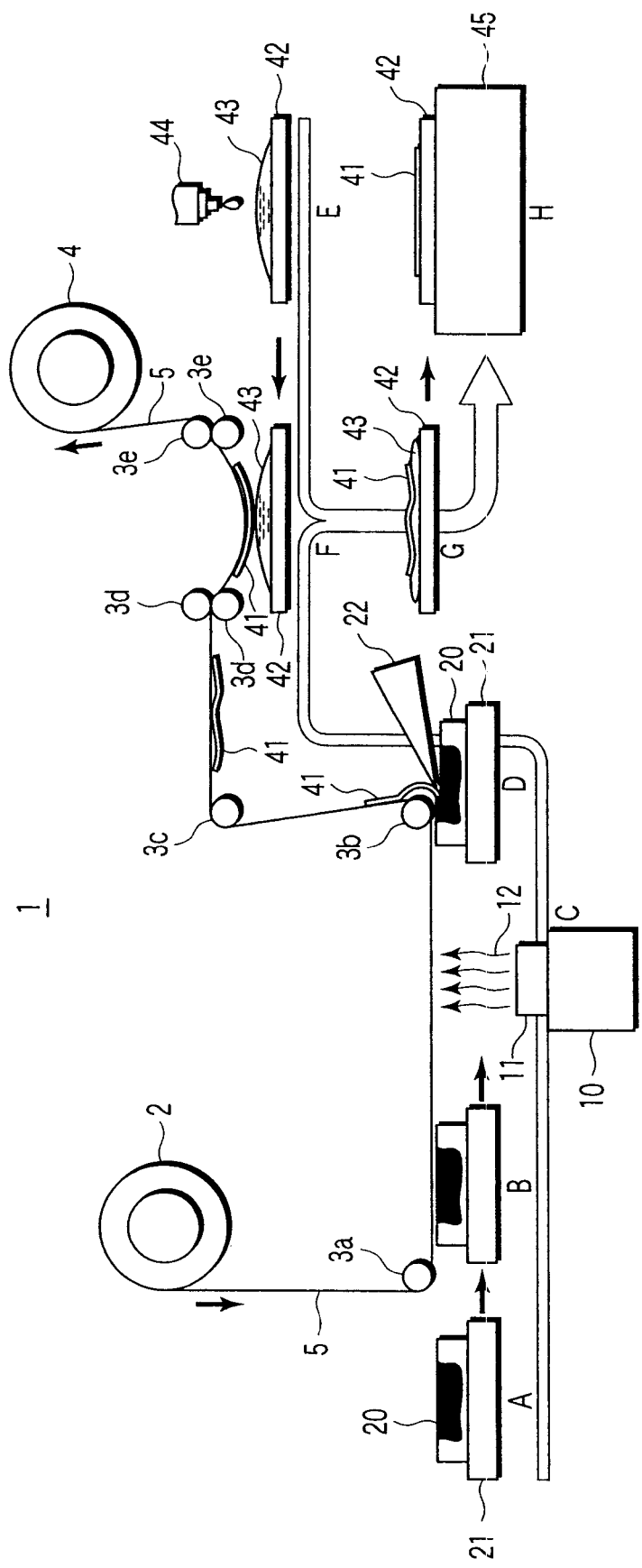
FIG. 1 is a schematic constitution block diagram showing a sample slice preparation device in a first embodiment of the present invention.

A device of a first embodiment of the present invention will be described with reference to FIG. 1.

A sample slice preparation device 1 includes: a feeding reel 2 to feed out a carrier tape 5 which functions as an auxiliary slicing member; and a windup drum 4 which winds up the carrier tape 5. When the windup drum 4 is rotated by a tape driving mechanism, the carrier tape 5 is fed as a slicing unit along an operation line of a microtome 21.

From an upstream side toward a downstream side of a movement path of the carrier tape 5, in a position between stages A and B, a guide roller 3a is disposed which changes a direction of the carrier tape 5 fed out of the feeding reel 2 from a vertical direction to a horizontal direction. In a position corresponding to stage C, a humidifier 10 is disposed. In a position corresponding to stage D, there are arranged a slicing unit (microtome) 21 provided with a knife 22 and a guide roller 3b which changes the direction of the carrier tape 5 from the horizontal direction to the vertical direction. In a position corresponding to stage E, a water dripping mechanism 44 is disposed as transfer means. In a position ranging from stage E to stage G, a conveyance robot 80 (see FIG. 4) is disposed as slide glass conveyance means. In a position corresponding to stage H, there is disposed an extension unit 45 having a hot plate 46.

The humidifier 10 has a nozzle 11 which opens upwards, and is disposed under a carrier tape movement path in a state in which a distance from this nozzle 11 to the carrier tape 5 is adjusted into a predetermined interval. Water vapor generated in the humidifier 10 is blown from the nozzle 11, and blown against the underside of the carrier tape 5 to wet the carrier tape 5. To achieve satisfactory impartment of moisture onto the carrier tape 5, it is preferable that the surface of the carrier tape 5 is hydrophilic. It is also preferable that the water vapor generated by the humidifier 10 is saturated or oversaturated at room temperature under an atmospheric pressure. It is to be noted that in the humidifier 10, there is usable any of an ultrasonic spray system, a jet spray system, a heating system and a system in which two or more of them are used together.

In a state in which a solid specimen 20 is mounted on an operation base of the microtome 21, the microtome is moved in a horizontal direction shown by an arrow in the diagram by a conveyance mechanism (not shown) along a feeding path of the carrier tape 5. The solid specimen 20 is constituted by burying, freezing and hardening a test body such as a living specimen in an embedding material such as paraffin.

The water dripping mechanism 44 is transfer means for transferring a slice 41 from the carrier tape 5 onto a slide glass 42. In the stage E, water is dripped from the water dripping mechanism 44 onto the slide glass 42 to form a water film 43, the slide glass 42 is conveyed to stage F by the slide glass conveyance means, and positioned right under a horizontal pass line of the carrier tape 5, the slide glass 42 is pressed onto the slice 41 attached to the tape 5, and the slice 41 is transferred from the carrier tape 5 onto the slide glass 42 by an adsorbing force of the water film 43.

Next, there will be described the extension unit and the slide glass conveyance means with reference to FIG. 4.

The hot plate 45 includes: the mounting surface 46 on which the slide glass 42 provided with the slice is to be mounted; and a heater 47 buried right under this mounting surface 46, and the hot plate functions as the extension unit. The heater 47 is connected to a heater power supply 48 having an operation controlled by a controller 50. A temperature sensor 49 is disposed right under the heater 47, the temperature of the hot plate 45 is detected, and a temperature detection signal is sent to an input section of the controller 50. The controller 50 controls an operation to supply power from the heater power supply 48 to the heater 47 based on an input signal. Accordingly, the slide glass 42 provided with the slice is heated at a desired temperature on the hot plate 45.

Figure 5:
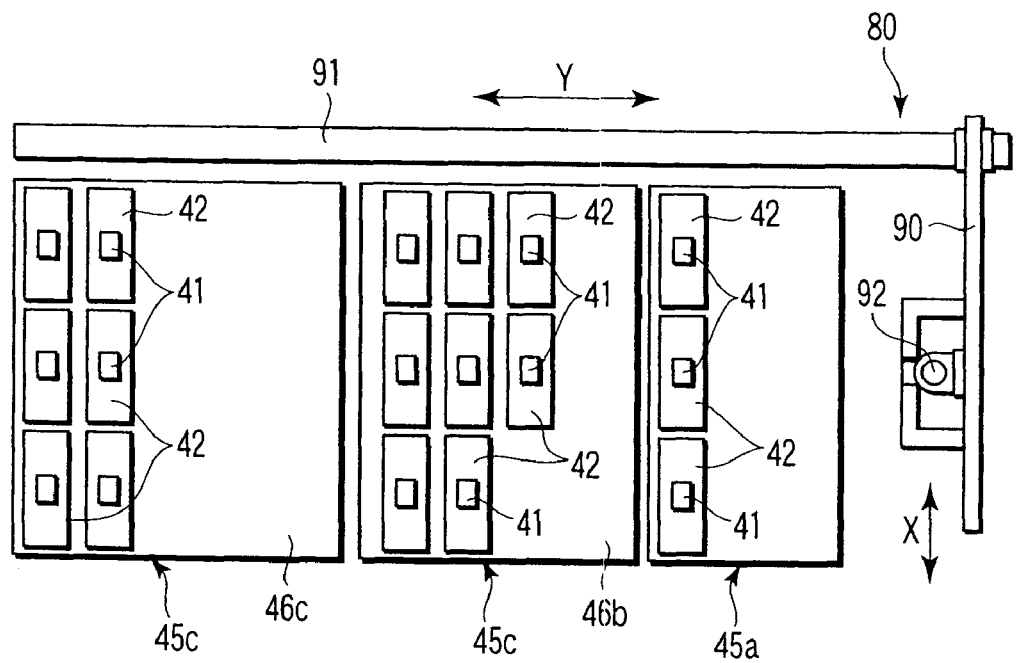
FIG. 5 is a plan view showing the conveyance robot and an extension unit.
Figure 6:
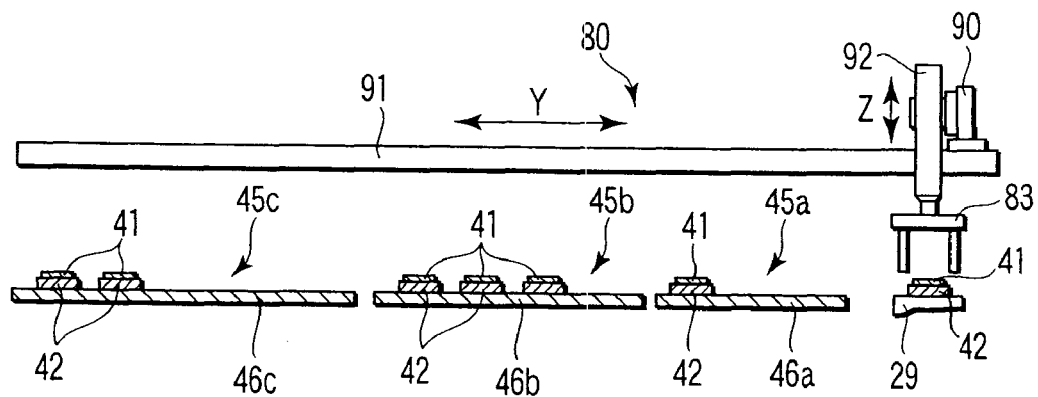
FIG. 6 is a side sectional view showing the conveyance robot and the extension unit.

As shown in FIGS. 5 and 6, the conveyance robot 80 as the slide glass conveyance means is supported movably in directions of three axes XYZ by a robot drive mechanism 84 in order to convey the slide glass 42 provided with the slice from a transfer position to the extension unit, and the robot includes a robot hand 83 and a pair of finger members 81, 82. The pair of finger members 81, 82 are attached to a distant end of the robot hand 83 so that they are apart from each other at a predetermined interval, and they are movably supported by a linear slider mechanism (not shown). When the finger members 81, 82 are brought close to each other, the finger members 81, 82 abut on an outer peripheral end surface of the slide glass 42, and the slide glass 42 is sandwiched between one finger member 81 and the other finger member 82.

The conveyance robot 80 includes: an X-axis linear system 90 which extends in a longitudinal direction of the slide glass 42; a Y-axis linear system 91 which extends in a width direction of the slide glass 42; and a Z-axis linear system 92 which is liftable in a thickness direction of the slide glass 42. The respective linear systems 90, 91 and 92 are equipped with a linear guide rail, a ball screw and a servo motor. The robot hand 83 is movably supported by these linear systems 90, 91 and 92 of three axes.

The controller 50 shown in FIG. 4 functions as control means for controlling an operation of the robot drive mechanism 84. In accordance with the slide glass 42 provided with the slice, the controller 50 controls the operation of the conveyance robot 80 so that this slide glass 42 provided with the slice can be heated at an optimum temperature for an optimum time. That is, in accordance with a type or a sliced state of the slice 41, one of a plurality of extension units 45a, 45b and 45c different from one another in temperature is selected, and the slide glass 42 provided with the slice is mounted on the hot plate 45a (or 45b or 45c) of the selected extension unit. Furthermore, after the slide glass 42 provided with the slice is heated under predetermined conditions, the controller 50 controls the operation of the conveyance robot 80 in order to take the glass out of the extension unit.

Next, there will be described a case where a sample slice is prepared using the device of the present embodiment with reference to FIGS. 1 and 2A to 2F.

The solid specimen 20 is set onto the mounting base of the microtome 21, and this is conveyed to stage D and positioned. Subsequently, the feeding reel 2 and the windup drum 4 are driven, respectively, the carrier tape 5 is fed at a predetermined speed, water vapor is sprayed from the humidifier 10 to the carrier tape 5, and moisture is imparted to the underside of the tape 5. The water vapor is brought into at least a saturated or oversaturated state in the nozzle 11 of the humidifier 10. Therefore, when the tape 5 having the hydrophilic surface comes into contact with the water vapor, the tape is easily wetted.

Figure 2A:
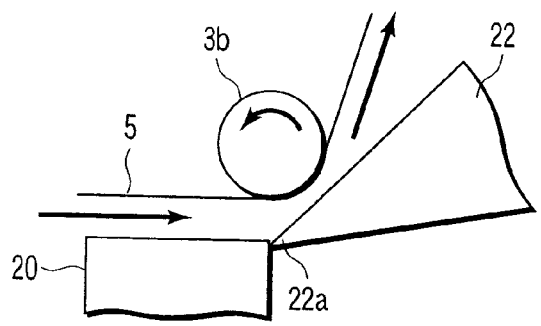
FIGS. 2A to 2F are step diagrams showing a procedure to sample a slice by use of the device of the first embodiment.
Figure 2B:
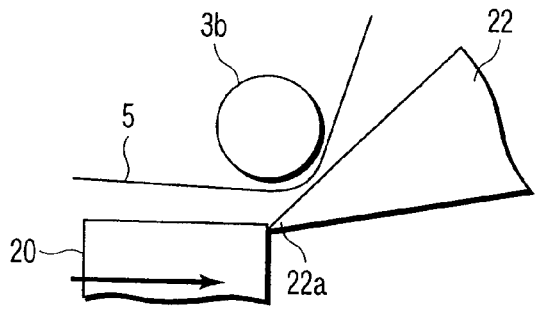

As shown in FIG. 2A, when the carrier tape 5 is fed from the feeding reel 2 to above (above the stage D) the solid specimen 20 on a conveyance base, and a portion wetted with the water vapor reaches the press roller 3b, as shown in FIG. 2B, the feeding of the tape 5 is stopped, whereas the feeding of the solid specimen 20 is started.

Figure 2C:
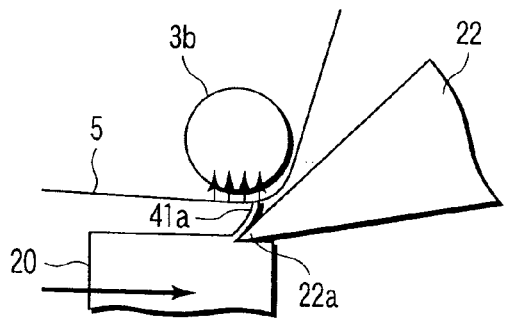
Figure 2D:
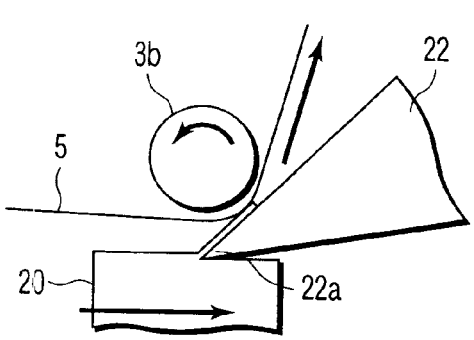

When the solid specimen 20 is fed toward the knife 22, the solid specimen 20 is accordingly sliced. With the feeding of the solid specimen 20, the slice 41 extends upwards to the tape 5. As shown in FIG. 2C, at the same time or immediately after a distant end 41a of the slice comes into contact with the tape 5, the feeding of the tape 5 is restarted as shown in FIG. 2D. This tape feeding restart timing may be set to a timing after a predetermined time uniformly elapses from the tape feeding stop time, a time when a sensor (not shown) detects that the distant end 41a of the slice has come into contact with the tape 5, or a timing after a predetermined time uniformly elapses from the detection time.

Figure 2E:
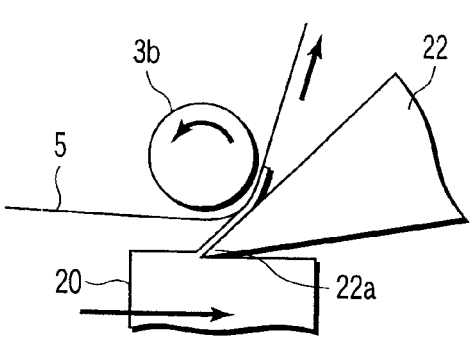

After the distant end 41a of the slice is adsorbed by the tape 5, the tape 5 is wound up at such a windup speed V2 that a speed ratio on percentage is 80 to 90% with respect to a slicing speed V1, and the slice 41 is sampled onto the tape 5 as shown in FIG. 2E. At this time, if the percentage of a speed ratio V2/V1 deviates from a range of 80 to 90%, a shape defect (non-uniformity of thickness, crease, shrinkage) of the slice 41 is easily generated. Therefore, the controller 50 controls both of the speeds V1, V2 with high precision. Specifically, the controller 50 controls a feeding speed of the conveyance base of the microtome 21, a speed at which the tape is fed from the feeding reel 2, a speed at which the tape is wound up by the windup drum 4, position adjustment of the roller 3b and the like, respectively.

Figure 2F:
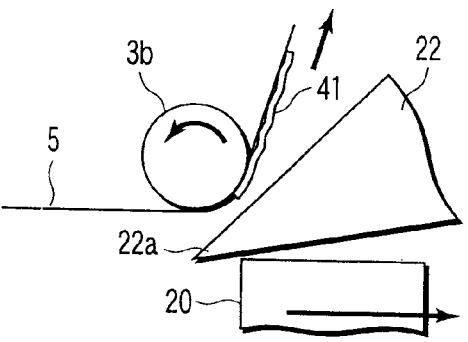

After the slicing is completed, as shown in FIG. 2F, the slice 41 completely shifts onto the tape 5, and is conveyed together with the tape 5 toward the stage F. When the slice 41 reaches the stage F, the feeding of the tape 5 is stopped, operations of the windup reel 4 and rollers 3d, 3e are further controlled, and the tape 5 between the rollers 3d and 3e is loosened as shown in FIG. 1. Moreover, the slide glass 42 provided with the water film 43 is raised, the slice 41 attached to the tape 5 is brought into contact with the water film 43, and the slice 41 is transferred from the tape 5 onto the slide glass 42 by the adsorbing force of the water film 43 (transference step). It is to be noted that the water film 43 on the slide glass 42 is formed by dripping an appropriate amount of water from the water dripping mechanism 44 onto the top of the slide glass 42 in stage E. The slide glass 42 provided with the water film 43 is conveyed from stage E to stage F at a predetermined timing by the conveyance robot 80.

After transferring the slice 41, the slide glass 42 provided with the slice 41 is conveyed to the extension unit 45 (45a, 45b or 45c) of stage H by the conveyance robot 80, and this glass is mounted on the hot plate of any desired extension unit. Moreover, the slide glass 42 provided with the slice 41 is heated at a predetermined temperature, the slice 41 is extended, and crease or shrinkage is removed from the slice 41.

For example, the slide glass 42 provided with the slice 41 is mounted on a hot plate 46a of the first extension unit 45a, and heated on conditions of a predetermined temperature and a predetermined time. The slide glass 42 provided with the slice 41, which has been heated in the first extension unit 45a, is conveyed out by the conveyance robot 80 after elapse of an extension time individually set by the controller 50. Thereafter, if necessary, the slide glass 42 provided with the slice 41 is conveyed into the second extension unit 45b, and further subjected to an extension treatment on different conditions.

While the sensor 49 detects the temperature, the controller 50 controls the power supply to the hot plate. After heating and holding the slide glass 42 provided with the slice 41 at at a temperature of, for example, 50±2° C. for about two minutes in the first extension unit 45a, this glass is conveyed into the second extension unit 45b, and heated and held at a temperature of, for example, 30±2° C. for about 30 minutes. When the extension treatment is performed in a stepwise manner for such a long time, the slice 41 has a smooth surface without any crease or shrinkage. It is to be noted that a lot-temperature heating time of a second stage in the second extension unit 45b can further be extended up to 24 hours, and shortened down to ten minutes. Instead of the extension unit having the hot plate, the slide glass 42 provided with the slice 41 may be disposed in a constant-temperature tank and warmed (heated) for a certain time.

In this manner, a non-dyed sample slice is finished. Finally, through a dyeing step and a sealing step of covering the sample with cover glass, the dyed sample slice is obtained.

According to the present embodiment, there is realized an automation technology in which the slice adsorbed by the water film is conveyed together with the carrier tape to the slide glass, and the slice is moved (transferred) from the tape onto the slide glass to form the sample. In consequence, it is possible to largely reduce a ratio of dependence on a manual operation in a pathological tissue inspection or the like.

SECOND EMBODIMENT

Figure 7:
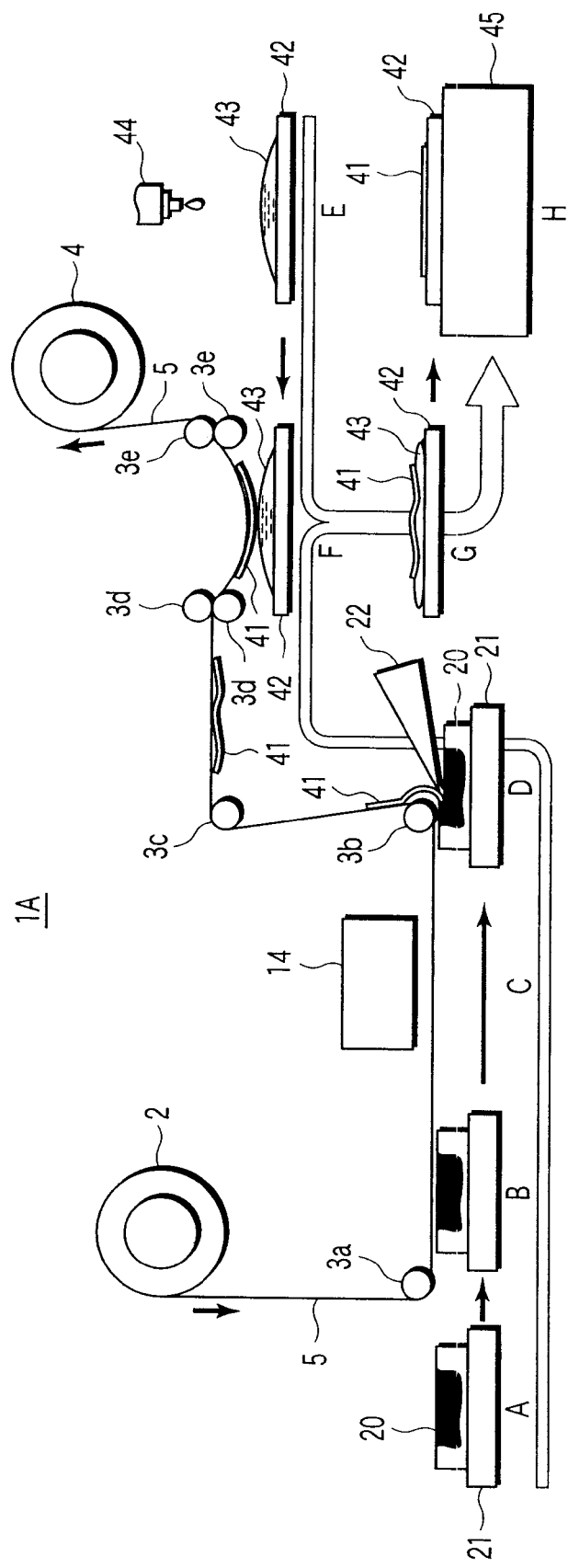
FIG. 7 is a schematic constitution block diagram showing a sample slice preparation device in a second embodiment of the present invention.

Next, a second embodiment will be described with reference to FIG. 7. It is to be noted that there is omitted description of a redundant part of the present embodiment with respect to the above embodiment.

In the second embodiment, a sample slice preparation device 1A includes a cooler 14 as moisture imparting means. The cooler 14 may be an air conditioner which blows off cold air having its temperature adjusted or a radiation cooling plate which radiation (emission)-cools a periphery. A power supply of the cooler 14 is connected to an output section of a controller 50. The cooler 14 is disposed above a pass line of a carrier tape 5 in stage C.

There will be described a case where a sample slice is prepared using the device 1A of the present embodiment.

A solid specimen 20 is set on a mounting base of a microtome 21, and this is conveyed to stage D and positioned. Next, a feeding reel 2 and a windup reel 4 are driven, respectively, and the carrier tape 5 is fed at a predetermined speed. Moreover, cold air (e.g., cold air having its temperature adjusted at 5° C.) is blown from the cooler 14 (air conditioner) toward the tape 5 to cool the tape 5. Accordingly, moisture contained in the atmosphere is condensed on the surface of the tape 5 to wet the tape 5. It is to be noted that the humidifier 10 of the first embodiment may be combined with the cooler 14 for use. When the cooler and the humidifier are combined and used in this manner, water drops can further firmly be imparted to the surface of the tape 5.

Subsequently, when the carrier tape 5 is fed from the feeding reel 2 to above (above stage D) the solid specimen 20 on a conveyance base, and a portion wetted with water vapor reaches a press roller 3b, the feeding of the tape 5 is stopped, whereas the feeding of the solid specimen 20 is started. When the solid specimen 20 is fed toward the knife 22, the solid specimen 20 is accordingly sliced. With the feeding of the solid specimen 20, a slice 41 extends upwards to the tape 5. At the same time or immediately after a distant end 41a of the slice comes into contact with the tape 5, the feeding of the tape 5 is restarted (see FIGS. 2C and 2D).

After the distant end 41a of the slice is adsorbed by the tape 5, the tape 5 is wound up at such a windup speed V2 that a speed ratio on percentage is 80 to 90% with respect to a slicing speed V1, and the slice 41 is sampled onto the tape 5. At this time, if the percentage of a speed ratio V2/V1 deviates from a range of 80 to 90%, a shape defect (non-uniformity of thickness, crease, shrinkage) of the slice 41 is easily generated. Therefore, the controller 50 controls both of the speeds V1, V2 with high precision.

After the slicing is completed, the slice 41 completely shifts onto the tape 5, and is conveyed together with the tape 5 toward stage F. When the slice 41 reaches stage F, the feeding of the tape 5 is stopped, operations of the windup reel 4 and rollers 3d, 3e are further controlled, and the tape 5 between the rollers 3d and 3e is loosened as shown in FIG. 1. Moreover, a slide glass 42 provided with a water film 43 is raised, the slice 41 attached to the tape 5 is brought into contact with the water film 43, and the slice 41 is transferred from the tape 5 onto the slide glass 42 by an adsorbing force of the water film 43 (transfer step). It is to be noted that the water film 43 on the slide glass 42 is formed by dripping an appropriate amount of water from a water dripping mechanism 44 onto the top of the slide glass 42 in stage E. The slide glass 42 provided with the water film 43 is conveyed from stage E to stage F at a predetermined timing by a conveyance robot 80.

After transferring the slice 41, the slide glass 42 provided with the slice 41 is conveyed to an extension unit of stage H by the conveyance robot 80, and this glass is mounted on a hot plate of any desired extension unit. Moreover, the slide glass 42 provided with the slice 41 is heated at a predetermined temperature, the slice 41 is extended, and crease or shrinkage is removed from the slice 41. In this manner, a non-dyed sample slice is finished. Finally, through a dyeing step and a sealing step of covering the sample with cover glass, the dyed sample slice is obtained.

According to the present embodiment, since minimum water required for adsorbing the slice by the tape is imparted to the tape without excessively wetting the carrier tape, in the transfer step, the slice can easily be transferred from the tape onto the slide glass.

THIRD EMBODIMENT

Next, a third embodiment will be described with reference to FIGS. 8A, 8B, 8C and 8D. It is to be noted that there is omitted description of a redundant part of the present embodiment with respect to the above embodiment.

In the third embodiment, a sample slice preparation device 1B includes three movable bars 32, 33 and 34 and one fixed roll 31 as transfer means. Each of the movable bars 32, 33 and 34 is movably supported so that a position can be changed by a cylinder mechanism (not shown).

The fixed roll 31 is substantially disposed in parallel to face the first movable bar 32 in a predetermined position under the first movable bar 32 in stage F, and constantly guides the tape 5 in the same position. The position of the fixed roll 31 does not change, but the first movable bar 32 is displaced until the bar abuts on the fixed roll 31 as shown in FIG. 8B.

The second movable bar 33 and the third movable bar 34 are positioned apart from the fixed roll 31/the first movable bar 32 as much as a predetermined distance in stage F, are substantially arranged in parallel to face each other, and guide the tape 5 toward a windup reel 4. The second movable bar 33 and the third movable bar 34 are displaced from fixed positions shown in FIG. 8A, respectively, as shown in FIGS. 8B, 8C and 8D.

Next, there will be described a case where a slice 41 is transferred from the tape 5 onto a slide glass 42 by use of the device 1B of the present embodiment.

The resultant slice 41 is fed to stage F in a state in which the slice 41 is attached to the tape 5 as shown in FIG. 8A. Where the slice 41 is positioned right above the slide glass 42 provided with a water film 43, the windup of the tape 5 by the reel 4 is stopped. As shown in FIG. 8B, the first movable bar 32 is lowered, and the tape 5 is sandwiched between the first movable bar 32 and the fixed roll 31. At this time, the third movable bar 34 is simultaneously moved toward the second movable bar 33, and as shown in FIG. 8B, the tape 5 is sandwiched between the second movable bar 33 and the third movable bar 34.

Next, in a state in which the tape 5 is sandwiched, as shown in FIG. 8C, the second movable bar 33 and the third movable bar 34 are both displaced obliquely downwards, and the slice 41 attached to the tape 5 is brought into contact with the water film 43 on the slide glass 42.

Next, in a state in which the tape 5 is sandwiched, as shown in FIG. 8D, the second movable bar 33 and the third movable bar 34 are both displaced obliquely upwards, and the tape 5 is detached from the slide glass 42. The slice 41 shifts from the tape 5 onto the slide glass 42 by the adsorbing force of the water film 43.

After the slide glass 42 provided with the slice is conveyed to the hot plate 45, the sandwiched tape 5 is released to return the first to third movable bars 32, 33 and 34 to the respective fixed positions. As shown in FIG. 8A, the windup of the tape 5 by the windup reel 4 is restarted.

When such an operation is repeated, the slice 41 is smoothly transferred from the tape 5 onto the slide glass 42.

According to the present embodiment, it is possible to largely reduce frequency of generation of a disadvantage that a part of the slice remains on a carrier tape side. In consequence, breakage is hardly generated in the slice, and a slice having a satisfactory shape can be obtained.

COMPARATIVE EXAMPLE

Next, there will be described transfer means of a comparative example with reference to FIGS. 9A, 9B, 9C and 9D. It is to be noted that there is omitted description of a redundant part of the present example with respect to the above embodiments.

A sample slice preparation device 1C of the comparative example includes one movable bar 62 and one fixed roll 61 as transfer means. The movable bar 62 is movably supported by a cylinder mechanism (not shown) so that a position can be changed.

The fixed roll 61 is substantially disposed in parallel with the movable bar 62 in a predetermined position under the movable bar 62 in stage F, and constantly guides the tape 5 in the same position. The position of the fixed roll 61 does not change, but the movable bar 62 is displaced in a stepwise manner as shown in FIGS. 9B, 9C and 9D.

Next, there will be described a case where a slice 41 is transferred from the tape 5 onto the slide glass 42 by use of the device 1C of the present example.

Figure 9D:
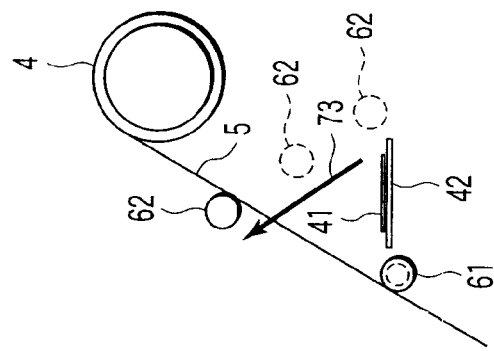
FIGS. 9A to 9D are step diagrams showing a procedure to transfer a slice onto a slide glass by use of a conventional sample slice preparation device as a comparative example.
Figure 9C:
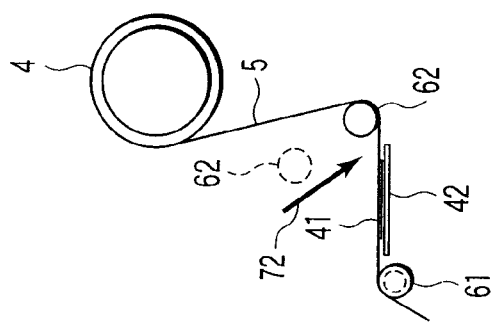
Figure 9B:
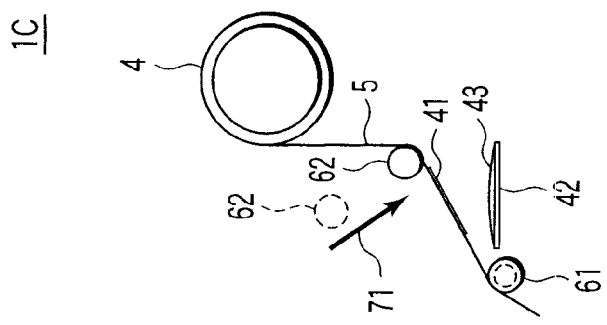
Figure 9A:
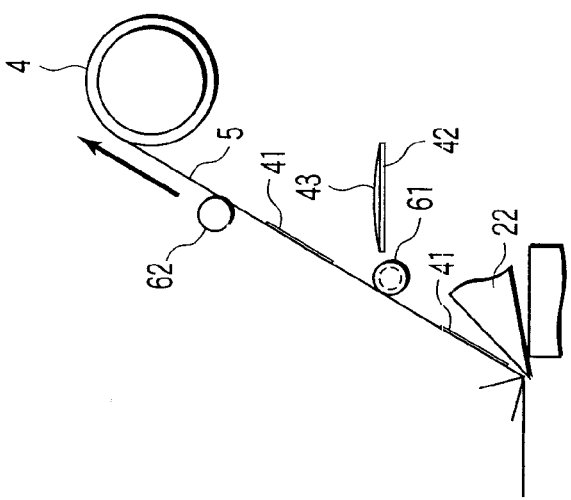
Figure 10A:
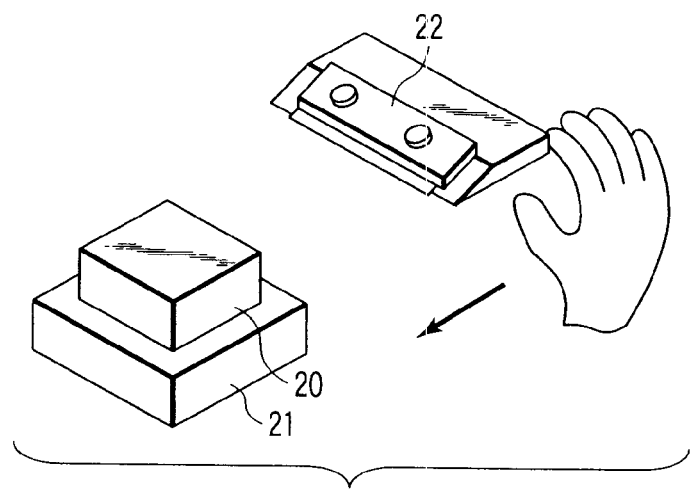
FIGS. 10A to 10C are perspective views showing a procedure to prepare a slice by use of a conventional sliding microtome.
Figure 10B:
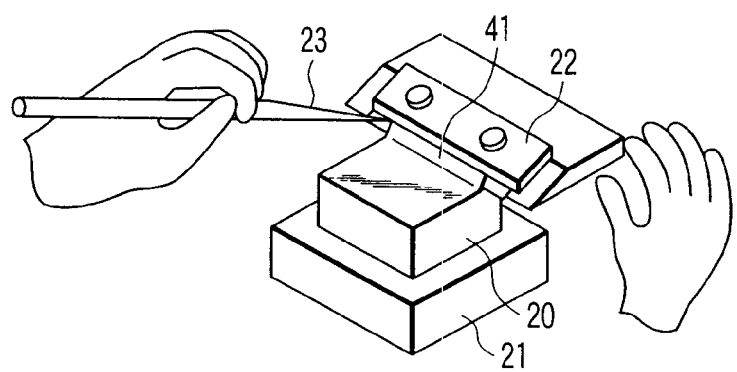
Figure 10C:
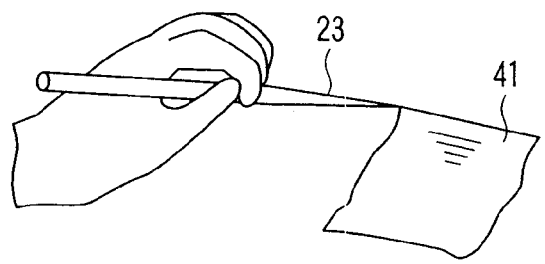

The resultant slice 41 is fed to the stage F in a state in which the slice is attached to the tape 5 as shown in FIG. 9A. When the slice 41 is positioned above the slide glass 42 provided with a water film 43, windup of the tape 5 by a reel 4 is stopped, and as shown in FIG. 9B, the movable bar 62 is displaced obliquely downwards to push the tape 5 downwards. Furthermore, as shown in FIG. 9C, the movable bar 62 is displace obliquely downwards, and the tape 5 is pushed downwards until the slice 41 comes into contact with the water film 43 on the slide glass 42.

Subsequently, as shown in FIG. 9D, the movable bar 62 is returned obliquely upwards to a fixed position to detach the tape 5 from the slide glass 42. The slice 41 shifts from the tape 5 onto the slide glass 42 by an adsorbing force of the water film 43. After the slide glass 42 provided with the slice is conveyed to an extension unit 45, as shown in FIG. 9A, the windup of the tape 5 by the windup reel 4 is restarted. When such an operation is repeated, the slice 41 is transferred from the tape 5 onto the slide glass 42.

According to the transfer means of the comparative example, there is generated a disadvantage that a part of the slice remains on a carrier tape side, break or the like is generated in the slice, and the slice having a shape defect sometimes results. It has found that the transfer means of the comparative example is uncertain as compared with the transfer means of the device of the above third embodiment.

The present invention can be utilized in preparation of the sample slice for use in scientific specimen analysis or a medical or biological analysis such as microscopic observation of a living specimen.

According to the present invention, there is realized an automation technology in which the slice adsorbed by the water film is conveyed together with the auxiliary slicing member to the slide glass, and the slice is transferred as the sample from the auxiliary slicing member onto the slide glass, and it is possible to largely reduce a ratio of dependence on the manual operation in pathological tissue inspection or the like.

What is claimed is:

1. A sample slice preparation device which slices, by a knife, a solid specimen constituted by embedding an original sample as a slice object with an embedding material to prepare a sample slice, the device comprising:
    a slicing unit which moves the solid specimen and the knife with respect to each other to slice the solid specimen into a predetermined slice thickness by the knife;
    moisture imparting means for imparting moisture to a tape-like auxiliary slicing member;
    slice conveyance means for adsorbing the resultant slice by an adsorbing force of the moisture imparted to the auxiliary slicing member to feed out the slice;
    transfer means for applying water to the surface of a slide glass to transfer the slice from the auxiliary slicing member onto the slide glass by the adsorbing force of applied water;
    an extension unit which heats the slide glass having the slice adsorbed thereon to evaporate the moisture, thereby extending the slice;
    and slide glass conveyance means for conveying the slide glass provided with the slice.

2. The device according to claim 1, wherein the moisture imparting means is a humidifier which sprays mist-like water toward the auxiliary slicing member.

3. The device according to claim 1, wherein the moisture imparting means is a cooler which locally cools the auxiliary slicing member and a peripheral region of the member to condensate moisture in the atmosphere onto the auxiliary slicing member.

4. The device according to claim 1, wherein the transfer means is a water dripping mechanism which drips warm water at a temperature of 30 to 50° C. onto the slide glass.

5. The device according to claim 1, wherein the transfer means drips and applies water at room temperature onto the slide glass, and then the extension unit heats water on the slide glass to obtain warm water at a temperature of 30 to 50° C.

6. The device according to claim 1, further comprising:
    control means for controlling the slice conveyance means to feed out the auxiliary slicing member at a speed ratio of 80 to 90% with respect to a slicing speed of the slicing unit, after one end of the slice is adsorbed by the auxiliary slicing member.

7. The device according to claim 1, further comprising:
    control means for controlling the slide glass conveyance means to take out the slide glass provided with the slice from the extension unit, after the slide glass provided with the slice is heated by the extension unit.

* * * * *